United States Patent [19]
Turkel et al.

[11] Patent Number: 5,257,632
[45] Date of Patent: Nov. 2, 1993

[54] COAXIAL BONE MARROW BIOPSY CORING AND ASPIRATING NEEDLE ASSEMBLY AND METHOD OF USE THEREOF

[75] Inventors: David H. Turkel; Thomas O. Bales, both of Miami; Frank A. Scarfone, Boca Raton; Milton L. Jackson, Jr., Miami, all of Fla.

[73] Assignee: Symbiosis Corporation, Miami, Fla.

[21] Appl. No.: 942,427

[22] Filed: Sep. 9, 1992

[51] Int. Cl.$^5$ .............................................. A61B 10/00
[52] U.S. Cl. ..................................................... 128/754
[58] Field of Search ............................... 128/752-754; 604/27, 28, 35, 49, 51, 164, 165, 167, 264, 272, 280

[56] References Cited

U.S. PATENT DOCUMENTS

| | | | |
|---|---|---|---|
| 4,356,828 | 11/1982 | Jamshidi | 128/754 |
| 4,403,617 | 9/1983 | Tretinyak | 128/754 |
| 4,469,109 | 9/1984 | Mehl | 128/753 |
| 4,793,363 | 12/1988 | Ausherman et al. | 128/754 |
| 4,838,282 | 6/1989 | Strasser et al. | 128/754 |
| 4,922,602 | 5/1990 | Mehl | 29/460 |
| 5,012,818 | 5/1991 | Joishy | 128/754 |

Primary Examiner—Max Hindenburg
Attorney, Agent, or Firm—David P. Gordon

[57] ABSTRACT

A bone marrow biopsy needle assembly for obtaining a bone marrow core biopsy and a bone marrow aspirate biopsy in a single procedure includes an outer aspiration sheath which closely surrounds a coaxial inner hollow coring needle, and a trocar which extends through the coring needle. A handle arrangement is provided to allow insertion into the bone of the central trocar, the core biopsy needle and the outer aspiration sheath as an assembly, and to further allow stable manipulation of each component of the system without displacing the outer aspiration sheath. After insertion of the combined system through the cortical bone layer, the trocar is withdrawn. Further pushing and, if desired, twisting of the remaining assembly forces a bone marrow core biopsy into the inner, coring needle. The coring needle is then withdrawn and the bone marrow core biopsy is pushed out in a retrograde manner. An aspiration syringe is then coupled to a luer slip on the aspiration sheath handle, and a liquid sample of marrow aspirate is obtained. Thus, a solid core of bone marrow and liquid marrow aspirate are obtained through a single entry into bone, thereby minimizing bone trauma and patient discomfort.

23 Claims, 4 Drawing Sheets

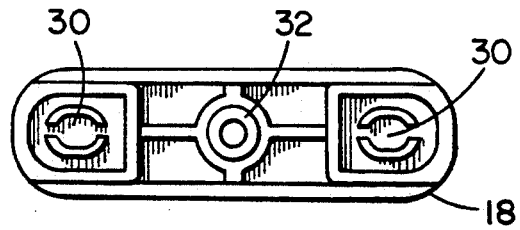
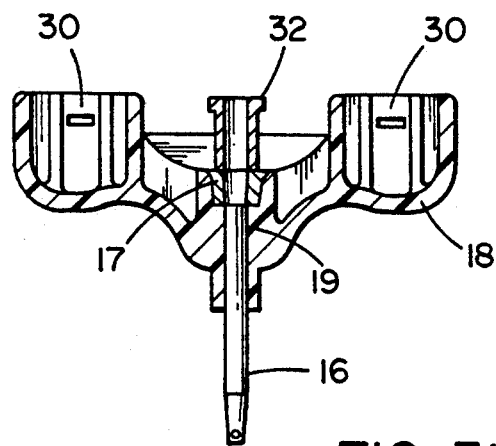
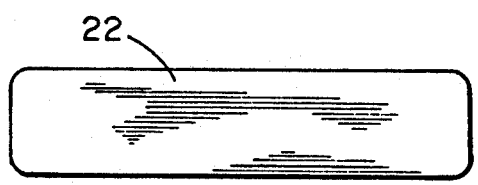
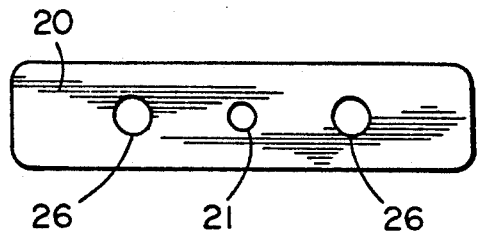
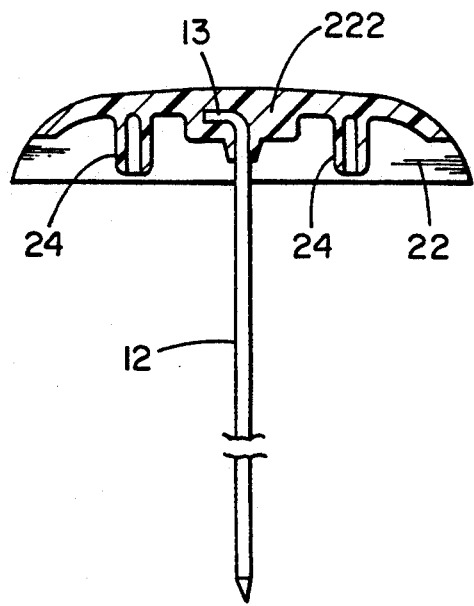
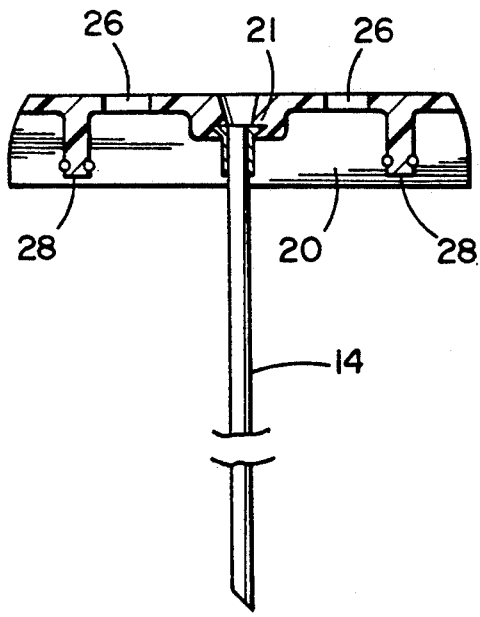

FIG. 5a
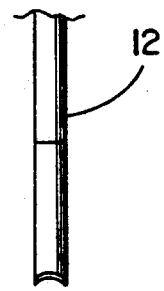
FIG. 5b
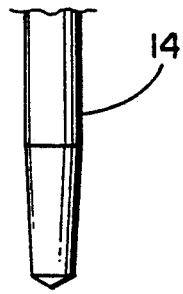
FIG. 5c
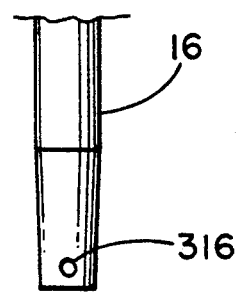
FIG. 6
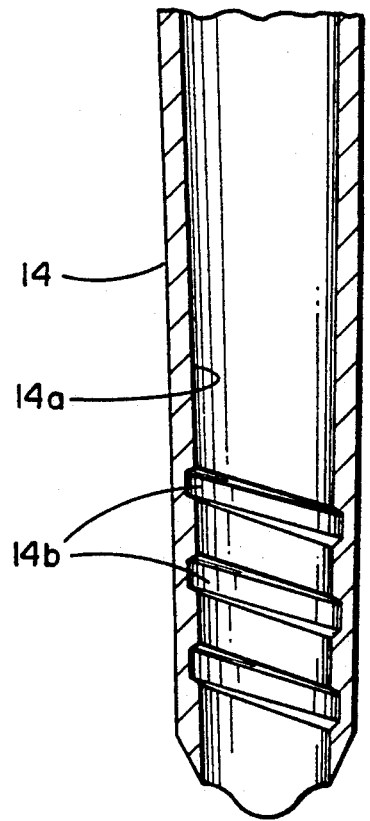

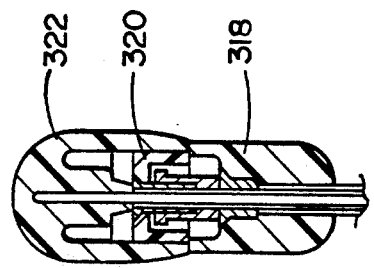
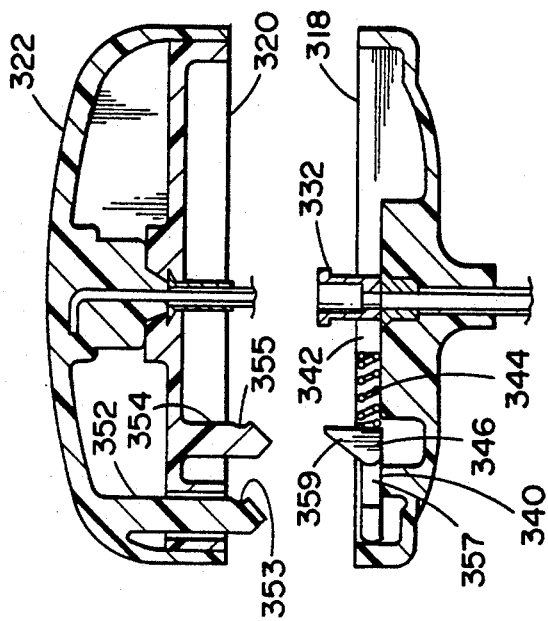
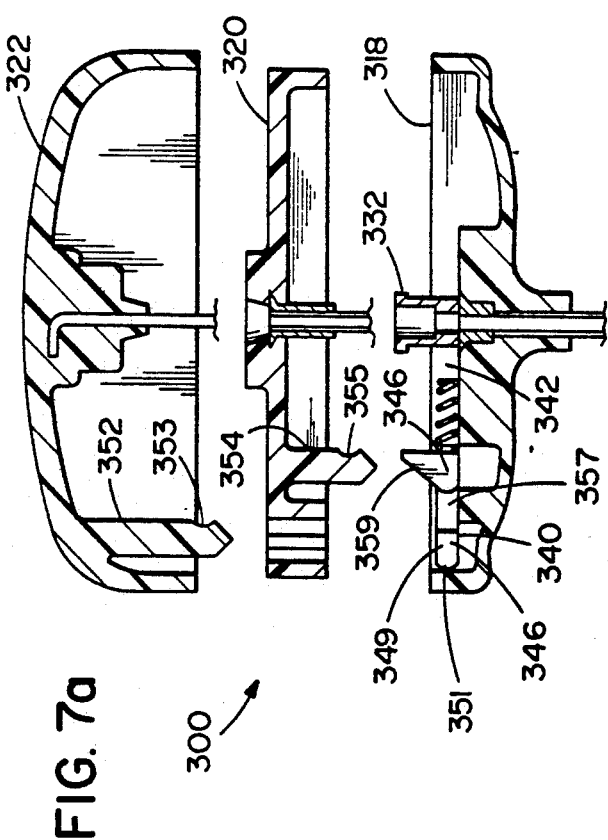
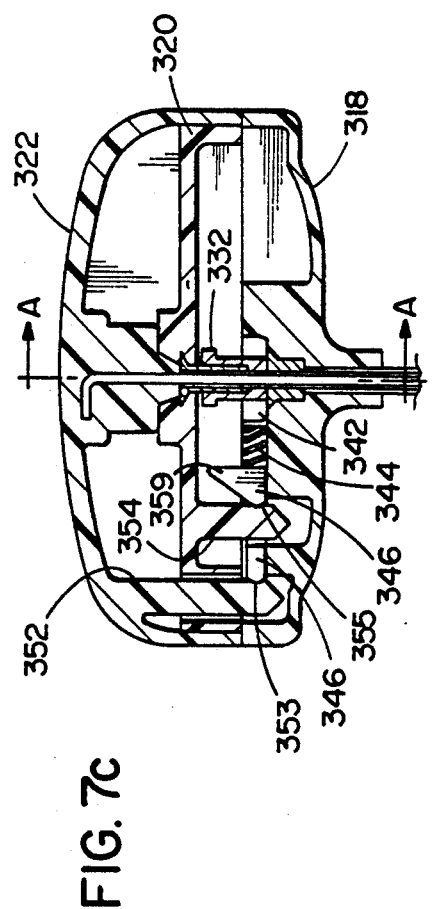

COAXIAL BONE MARROW BIOPSY CORING AND ASPIRATING NEEDLE ASSEMBLY AND METHOD OF USE THEREOF

BACKGROUND OF THE INVENTION

This invention relates to surgical biopsy needle instruments. More particularly, this invention relates to a coaxial needle for obtaining specimens of solid marrow core biopsy and fluid marrow aspirate in a single procedure.

Known biopsy needles generally include a cannula having a lumen extending therethrough, and a trocar or stylet which is removably inserted through the lumen of the cannula. The proximal ends of the cannula and trocar are provided with some type of gripping means and the distal ends of the cannula and trocar are sharpened to a bone piercing edge. In order to obtain a bone marrow specimen, the trocar and cannula are forced through the outer hard layer of the bone containing the marrow. Once the softer, internal region of the bone is reached, the trocar is withdrawn and a specimen is obtained by advancing the cannula further into the bone. The cannula containing the core sample of bone marrow is then carefully withdrawn so as to retain the marrow material.

The bone marrow biopsy procedure is quite painful to the patient and requires much exertion by the physician. Early problems with biopsy needles involved the sharpness of the cannula and trocar and the gripping means used so that the needle could be placed accurately and the bone could be penetrated quickly. U.S. Pat. No. 4,356,828, for example, discloses an improved finger gripping member and U.S. Pat. No. 4,403,617 discloses particular cutting edge configurations for the trocar and cannula.

Developments in the gripping means of the trocar and cannula continued with emphasis placed on the secure engagement of the trocar within the cannula and ease of use for the physician. U.S. Pat. Nos. 4,922,602; 4,838,282, 4,793,363 and 4,469,109 for example, disclose fairly elaborate interlocking systems between the trocar gripping means and the cannula gripping means and different shapes for the gripping means.

Other problems exist, however, with the known and recently improved biopsy needles. In particular, it is often necessary to obtain two types of specimens of bone marrow: a core sample as described above, and an aspirated sample. To obtain an aspirated sample, the cannula and trocar are inserted under pressure through the outer hard layer of a marrow containing bone. Once the softer, internal region of the bone is reached, the trocar is withdrawn and a specimen is obtained by connecting an aspirating syringe through the proximal end of the cannula and aspirating marrow fluid into the syringe. While both the aspiration and core sample procedures can be performed using the same needle, they do require two separate insertions and despite the improvements in needle sharpness and gripping means design, it is still quite painful to the patient and quite arduous for the physician.

U.S. Pat. No. 5,012,818 to Joishy discloses a "Two in One Bone Marrow Surgical Needle" which comprises an elongated needle with two heads at the proximal end with two portals entering into two parallel hollow lumens leading to two openings at the distal end. One of the lumens is larger and circular and the other is smaller and semilunar. The larger lumen is used to take a core sample specimen and the smaller lumen is used to take an aspirated specimen. While the provided arrangement overcomes the necessity of conducting two procedures to obtain a marrow core and an aspirated sample, it will be appreciated that because the lumens lie parallel to each other, the needle disclosed by Joishy is necessarily large in diameter. Indeed, this is a major drawback of the Joishy needle, as its use is more painful to the patient and requires more effort by the physician.

SUMMARY OF THE INVENTION

It is therefore an object of the invention to provide an coaxial biopsy needle assembly which allows the taking of both aspirated and core samples in a single procedure but which nevertheless has a relatively small diameter.

It is a further object of the invention to provide a handle arrangement on the biopsy coring and aspirating needle assembly to allow easy insertion and stable manipulation of the components of the needle assembly.

It is another object of the invention to provide a secure means for obtaining core samples whereby the core samples are retained while being extracted.

It is also an object of the invention to provide a handle arrangement on a dual function bone marrow biopsy needle where the aspiration needle cannot be assembled without the coring needle in place, and the aspirating needle cannot be removed before the coring needle is removed.

In accord with these objects which will be discussed in detail below, the bone marrow biopsy needle assembly of the present invention generally comprises an outer aspiration sheath or needle which is closely surrounding a coaxial inner hollow, distally tapered core biopsy needle which in turn closely surrounds a pointed central metallic trocar or stylet. Each of the aspiration sheath, coring needle, and trocar include a handle. The handle arrangement is provided to allow an easy insertion of the trocar, core biopsy needle, and outer aspiration sheath assembly into the bone, and to further allow stable manipulation and removal of each component of the system without displacing the outer aspiration sheath.

Preferred aspects of the bone marrow biopsy needle assembly include: the base of the core biopsy needle having internal scoring or threads designed to further hold the core of bone marrow; and a handle arrangement where the handle of the trocar is easily removed without removing the core biopsy needle assembly, and the handle of the core biopsy needle is removed without removing the aspirating needle assembly.

According to the method of the invention, after insertion of at least the trocar tip, and preferably the tips of all three elements of the combined assembly through the cortical bone layer of the patient, the central pointed trocar is withdrawn from the assembly. Further pushing of the needle assembly without the trocar forces a bone marrow core into the inner, distally tapered, coring needle. The pushing of the needle is preferably accompanied by a screw-like turning performed by the physician, which allows further retention of the bone marrow core due to the internal threads of the distally tapered needle. This inner needle is then withdrawn and the bone marrow core biopsy is pushed out in a retrograde manner. The outer sheath is stabilized during removal of the core biopsy needle by means of a special gripping mechanism. The outer sheath is then connected to an aspirating syringe by an airtight mating means such as a luer slip and a liquid sample of marrow aspirate is obtained. Thus, a solid core of bone marrow and liquid marrow aspirate are obtained through a single entry into the bone, using a compact system, and therefore minimizing bone trauma and patient discomfort.

Additional objects and advantages of the invention will become apparent to those skilled in the art upon reference to the detailed description taken in conjunction with the provided figures.

BRIEF DESCRIPTION OF THE DRAWINGS

FIGS. 2a and 2b are respectively cross-sectional and top plan views of the aspiration needle assembly of the bone marrow biopsy needle assembly of FIG. 1b;

FIGS. 3a and 3b are respectively cross-sectional and top plan views of the coring needle assembly of the bone marrow biopsy needle assembly of FIG. 1b;

FIGS. 4a and 4b are respectively cross-sectional and top plan views of the trocar assembly of the bone marrow biopsy needle assembly of FIG. 1b;

FIGS. 5a, 5b, and 5c respectively show perspective views or the distal portions of the trocar, the bone marrow biopsy needle, and the aspiration needle of FIGS. 4a, 3a, and 2a;

FIG. 6 shows a cross-sectional view of the bone marrow biopsy needle with internal threading for core retention;

FIGS. 7a, 7b, and 7c are respectively, an exploded cross-section view, a partially assembled cross-section view, and an assembled cross-section view of a second embodiment of the handle arrangement for the bone marrow biopsy needle assembly of the invention; and FIG. 7d is a cross-section along line A—A in FIG. 7b.

DETAILED DESCRIPTION OF THE PREFERRED EMBODIMENT

Figure 1A:
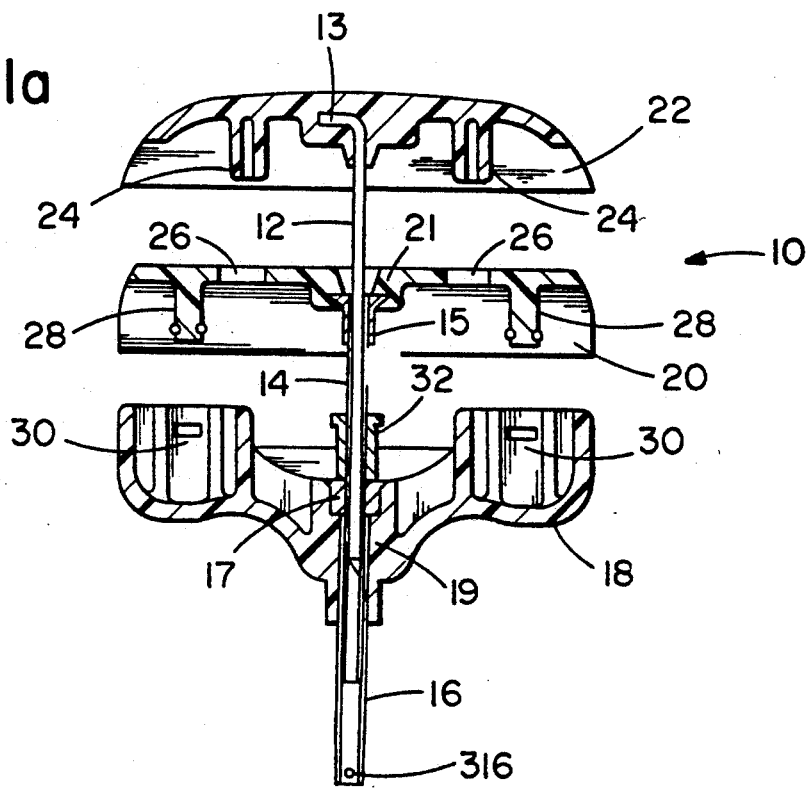
FIG. 1a is an exploded cross sectional view of one embodiment of the dual function bone marrow biopsy needle assembly of the invention during assembly.

Referring now to FIGS. 1a-1c, 2a, 2b, 3a, 3b and 4a, 4b the dual function bone marrow biopsy needle 10 of the invention includes an aspiration cannula 16 within which there is coaxially disposed a coring cannula 14 within which there is coaxially disposed a trocar (or stylet) 12. Each of these three coaxial parts is provided with a handle portion so that aspiration cannula 16 is provided with a first handle 18; coring cannula 14 is provided with a second handle 20, and trocar (or stylet) 12 is provided with a third handle 22.

The trocar handle 22 may be fixed to the trocar needle 12 in a known way, for example, by molding it about a bend 13 in needle 12. The coring handle 20 may be fixed to coring cannula 14 in any suitable manner such as by insert molding or such as by providing coring cannula 14 with a sleeve 15 which is affixed to the handle 20 at a throughbore 21 in the handle 20 such as by soldering. It is necessary to provide handle 20 with such a throughbore 21 so that trocar 12 may fit coaxially into coring cannula 14. The aspiration handle 18 likewise may be fixed to the aspiration cannula 16 in a similar way using throughbore 19 and sleeve 17 or by insert molding. It is also necessary in the aspiration handle that the throughbore 19 be coaxial with the throughbore 21 in handle 20 so that the trocar needle 12 and coring cannula 20 fit coaxially into aspiration cannula 16. Aspiration handle 18 is also ideally provided with a luer slip or luer lock 32 for connection with an aspirating syringe (not shown) which is used during aspiration of marrow through the aspiration cannula 16.

Each of the three handle portions of the assembly 10 is provided with interlocking mating means so that the three handle portions may be connected to each other in a secure manner. In a first embodiment, shown most clearly in FIGS. 1a, 1b, 2a, 3a, and 4a, the aspiration handle 18 is provided with an interlocking means 30 for disengageably mating with a first interlocking means 28 on the coring handle 20; and the coring handle is provided with a second interlocking means 26 for disengageably mating with an interlocking means 24 on the trocar handle 22. In this first embodiment, the interlocking mating means comprise projections 24, 28 and receiving sockets 26, 30, with the coring handle having both projections 28 for mating with sockets 30 of the aspiration handle, and receiving sockets 26 for mating with the projections 24 of the trocar handle 22. It should be appreciated that the projections and/or the sockets are sufficiently elastic to allow relatively easy mating and disengagement, but sufficiently inelastic to prevent undesired disengagement. It should also be appreciated that the coefficient of friction in the mating of the coring handle 20 with the aspiration handle 18 should be greater than the coefficient of friction in the mating of the trocar handle 22 with the coring handle 20. In this manner, trocar handle 22 can be disengaged from the coring handle 20 and removed without the coring handle 20 disengaging the aspiration handle 18.

Figure 1B:
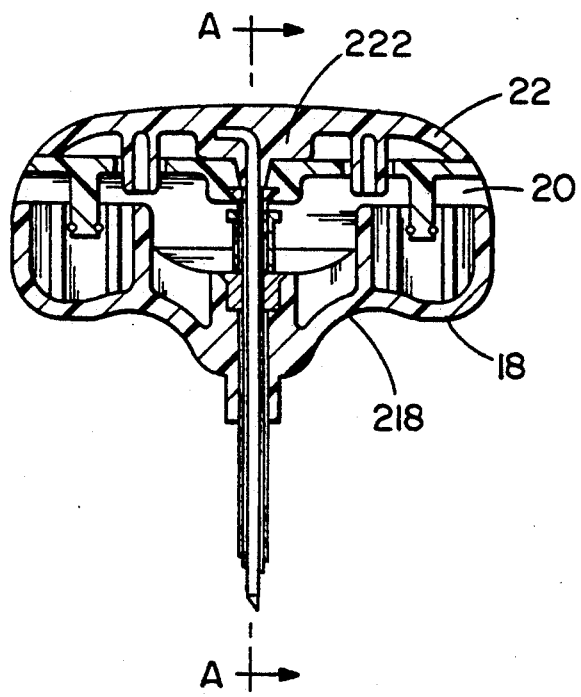
FIG. 1b is a cross-sectional view of the assembled bone marrow biopsy needle assembly of FIG. 1.
Figure 1C:
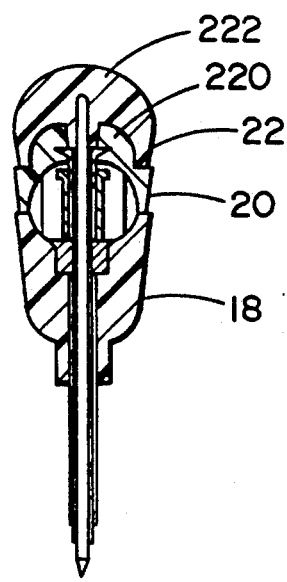
FIG. 1c is a cross section along line A—A in FIG. 1b.

Referring now to FIGS. 1b and 1c, it is seen that the three handles 18, 20, 22 interlock to form a single compact unit which fits easily and comfortably in the hand. Moreover, when the three pieces are assembled, trocar needle 12 extends beyond the distal tip of the coring cannula 14 which extends beyond the distal tip of the aspiration cannula 16. Ideally, and as shown in FIG. 1c, the trocar handle 22 is provided with a smooth curved top portion 222 which fits comfortably into the palm of the hand and aspiration handle 18 has a curved lower portion 218 against which fingers comfortably grip. The coring handle 20 is also provided with a smooth top 220 since after removal of the trocar needle 12 by its handle 22, the palm of the hand will rest against the top of coring handle 20 during the extraction of a core sample.

As seen in FIGS. 5a-5c, in the preferred embodiment of the invention, the distal ends of trocar needle 12, coring cannula 14, and aspiration cannula 16 are different. In particular, the trocar 12 is of smallest cross-section, is preferably solid in cross-section, and tapers to a sharp distal point. If desired, the trocar 12 may take the form of other trocars taught for use in bone marrow biopsy assemblies with an oblique concave face such as taught in U.S. Pat. No. 4,403,617, etc. The coring cannula 14, on the other hand, is hollow and of greater diameter than the trocar 12, thereby permitting the trocar 12 to be inserted therethrough in a close coaxial fit. As seen in FIG. 5b, the coring cannula 14 is also preferably tapered to form a distal point, and as seen in FIG. 6 the inside 14a of the coring cannula is likewise tapered somewhat in order to retain the bone marrow core. As aforementioned, and as seen in FIG. 6, the coring cannula 14 is preferably provided with internal scoring or threading 14b. It can be appreciated how this configuration of coring cannula aids in retention of the core sample when the cannula is withdrawn. Moreover, it can be appreciated how this configuration when used with a screw-like turning action allows for an easier extraction of the core sample.

Returning to FIG. 5c, the aspiration sheath or cannula 16 is seen to be hollow and to have a larger diameter than the coring cannula 14, as the coring cannula is inserted through the aspiration cannula 16 in a close coaxial fit. The distal end of the aspiration cannula 16 is preferably provided with a side port(s) 316 to improve aspiration characteristics.

A second embodiment for the handles of the biopsy needle assembly is shown in FIGS. 7a-7c. While the overall shape and size of the handles may appear similar to the design shown in the previous figures, the mating interlocking means between the different handles is different. An object of the second embodiment is to prevent the assembly and use of the biopsy needle assembly without the use of the bone marrow coring needle, as well as to prevent the inadvertent removal of coring handle 20 (and thus coring cannula 14) during the removal of the trocar handle 22.

In order to accomplish this object, the embodiment of the handle 300 shown in FIGS. 7a-7d provides a latching mechanism 340 located in the aspiration assembly handle 318. The latching mechanism 340 includes a slot 342 in the aspiration handle 318, a spring 344 located in slot 342 which is biased radially outwards from the center of the aspiration handle 318, an engaging pin 346 which rides in the slot 342 and which is coupled to and biased by the spring 344, and pins 352 and 354 extending downward from the trocar handle 322 and from the coring handle 320 into slot 342. Each of the pins 352 and 354 is provided with an indent 353 and 355, and engaging pin 346 is provided with a hole 357 perpendicular to its longitudinal axis, and a ramped protrusion 359 which starts at the hole 357 and extends upwards towards the coring handle 320. As seen in FIG. 7a, before the handles 318, 320 and 322 are assembled, the rounded end 349 of engaging pin 346 extends to the end 351 of slot 342 and blocks access of pin 352 of the trocar handle into the slot. Thus, the trocar and aspiration handles cannot be assembled together by themselves. However, when the coring handle is provided, pin 354 of the coring assembly engages the ramped protrusion 359 as seen in FIG. 7b. When the coring handle 320 is pushed downward, the pin 354 rides on the ramped protrusion 359 of the spring biased engaging pin 346 and pushes the pin 346 backward toward the center axis of the aspiration assembly. This movement continues until pin 354 extends through the hole 357 of the engaging pin 346 with the end of the protrusion 359 engaging the indent 355 in the pin 354 as seen in FIG. 7c. With the aspiration handle 318 and coring handle 320 so engaged, it will be appreciated that the engagement pin 346 no longer blocks access of pin 352 into slot 342. In fact, as the trocar handle 322 is moved down into position, pin 352 pushes the tip of engaging pin 346 slightly backward until engaging pin 346 can rest into indent 353. Preferably, indent 353 of pin 352 is not as deep as indent 355 of pin 354. Thus, when the trocar handle 322 is removed from the assembly by a force strong enough to force pin 352 out of engagement with the end of the engaging pin 346, the end of ramped protrusion 359 will still engage indent 355 of pin 354 and prevent inadvertent removal of the coring handle.

As seen best in FIGS. 7b and 7d, the nesting structure of the coring handle 320 and the trocar handle 322 provides additional assurance against inadvertent removal of the coring handle 320 upon removing the trocar handle 322. In particular, the width of the trocar handle 322 is greater than the coring handle 320, and trocar handle 322 is provided with a shell extension 382 which encompasses the coring handle 320 therein (except for an extending part of pin 354). Because the coring handle 320 does not have an external surface for gripping by the practitioner when the trocar handle 322 is in place, the coring handle 320 will remain in place when the trocar handle 322 is removed.

It is noted that the coring handle 320 of the second handle embodiment is provided with a through-hole 371 as seen best in FIG. 7a to permit the pin 352 of the trocar handle 322 to extend therethrough. It should be appreciated, however, that if desired, the coring handle 320 can be made small enough in width such that it does not need to accommodate pin 352. In such an arrangement, it may be desirable to have the shell extension 382 be of greater width and extend on both sides of pin 352.

It will be appreciated by those skilled in the art that the method of the invention relates directly to the provided apparatus assembly. In particular, with the bone marrow biopsy needle assembled, at least the trocar tip, and preferably the three tips of the assembly are first forced into and through the cortical bone layer of the patient. The central pointed trocar is then withdrawn by pulling on the trocar handle while holding the aspiration handle in place. The remaining assembly of the coring needle and handle and the aspiration needle and handle are then pushed to force bone marrow core into the inner, distally tapered, coring needle. The pushing of the needle is preferably accompanied by a screw-like turning performed by the physician, which allows further retention of the bone marrow core due to the internal threads of the distally tapered needle. This inner needle is then withdrawn by pulling on the coring handle and holding the aspiration handle in place. Typically, the bone marrow core biopsy is pushed out in a retrograde manner. An aspirating syringe with a luer is then connected to the luer slip of the aspirating handle, and a liquid sample of marrow is obtained. The aspiration cannula may then be withdrawn by pulling on the aspiration handle.

There have been described and illustrated herein coaxially disposed dual action bone marrow biopsy needle assembles with interlocking handles and methods of use pertaining thereto. While particular embodiments of the invention have been described, it is not intended that the invention be limited thereto, as it is intended that the invention be as broad in scope as the art will allow and that the specification be read likewise. Thus, while particular handle shapes have been disclosed, it will be appreciated that other shapes could be utilized. Also, while two different handle interlocking arrangements have been shown, it will be recognized that other types of interlocking mechanisms could be used with similar results obtained. Moreover, while particular configurations have been disclosed in reference to the distal ends of the trocar and cannulae, it will be appreciated that other configurations could be used as well. Furthermore, while the coring cannula has been disclosed as having a particular type of internal surface, it will be understood that different internal surfaces can achieve the same or similar function as disclosed herein. Therefore, it will be appreciated by those skilled in the art that yet other modifications could be made to the provided invention without deviating from its spirit and scope as so claimed.

We claim:

1. A bone marrow biopsy needle assembly, comprising:
   a) a hollow aspiration cannula having a distal tip;
   b) a hollow coring cannula having a distal tip, said hollow coring cannula extending substantially coaxially through said hollow aspiration cannula with said distal tip of said hollow coring cannula extending distally past said distal tip of said hollow aspiration cannula, said coring cannula being removable from said hollow aspiration cannula; and
   c) a trocar means having a distal tip, said trocar means extending substantially coaxially through said hollow coring cannula with said distal tip of said trocar means extending distally past said distal tip of said hollow coring cannula, said trocar means being removable from said hollow coring cannula.

2. A biopsy needle assembly according to claim 1, wherein:
   said hollow aspiration cannula, said hollow coring cannula, and said trocar means have respective proximal ends, with said proximal end of said coring cannula extending proximally past said proximal end of said aspiration cannula, and with said proximal end of said trocar means extending proximally past said proximal end of said coring cannula.

3. A biopsy needle assembly according to claim 2, further comprising:
   d) first handle means connected to said proximal end of said aspiration cannula;
   e) second handle means connected to said proximal end of said coring cannula, said second handle means for removing said coring cannula from said aspiration cannula; and
   f) third handle means connected to said proximal end of said trocar means, said third handle means for removing said trocar means from said coring cannula.

4. A biopsy needle assembly according to claim 3, wherein:
   said first handle means has first engagement means;
   said second handle means has second and third engagement means, said second engagement means for disengageably mating with said first engagement means; and
   said third handle means has fourth engagement means for disengageably mating with said third engagement means.

5. A biopsy needle assembly according to claim 4, wherein:
   said first and second engagement means mate with a first friction force,
   said third and fourth engagement means mate with a second friction force, said first friction force being greater than said second friction force.

6. A biopsy needle assembly according to claim 5, wherein:
   said first engagement means comprises a first projection extending from said first handle means, and said second engagement means comprises a first receiving socket in said second handle means.

7. A biopsy needle assembly according to claim 6, wherein:
   said third engagement means comprises a second projection extending from said second handle means, and said fourth engagement means comprises a second receiving socket in said third handle means.

8. A biopsy needle assembly according to claim 5, wherein:
   said third engagement means comprises a projection extending from said second handle means, and said fourth engagement means comprises a receiving socket in said third handle means.

9. A biopsy needle according to claim 3, wherein:
   said first handle means has first engagement means;
   said second handle means has second engagement means for disengageably mating with said first engagement means.

10. A biopsy needle according to claim 9, wherein:
    said first engagement means comprises a slot in said first handle, a biasing means in said slot, and a pin means coupled to said biasing means in said slot, said pin means being biased radially outward with respect to a longitudinal axis of said aspiration cannula, and
    said second engagement means extends into said slot and is disengageably mated by said pin means.

11. A biopsy needle according to claim 10, wherein:
    said second engagement means comprises a second pin means extending from said second handle means in a manner substantially parallel to said longitudinal axis of said aspiration cannula, said second pin means having an indent with which said pin means mates.

12. A biopsy needle according to claim 11, wherein:
    said radially biased pin means includes a ramped portion, and said second pin means rides down said ramped portion of said pin means and thereby pushes said biased pin means radially inward during assembly of said hollow aspiration cannula with said first handle means and said hollow coring cannula with said second handle means.

13. A biopsy needle according to claim 11, wherein:
    said third engagement means extends into said slot and is disengageably mated by said radially biased pin means, and
    said third engagement means comprises a third pin means extending from said third handle means in a manner substantially parallel to said second pin means, said third pin means having a second indent with which said pin means mates.

14. A biopsy needle according to claim 13, wherein:
    said first pin means has a hole through which said second pin means extends.

15. A biopsy needle according to claim 9, wherein:
    said third handle means has a shell portion, said shell portion extending around and over said second handle means.

16. A biopsy needle according to claim 9, wherein:
    said third handle means has a third engagement means for disengageably mating with said first engagement means.

17. A biopsy needle according to claim 16, wherein:
    said third handle means has a shell portion, said shell portion extending around and over said second handle means.

18. A biopsy needle assembly according to claim 1, wherein:
    said coring cannula has a scored inner surface.

19. A method for obtaining a bone marrow core biopsy and a bone marrow aspirate biopsy from a bone by utilizing a biopsy needle assembly having a hollow aspiration cannula having a distal tip and a first handle coupled to its proximal end, a hollow coring cannula extending substantially coaxially through the hollow aspiration cannula and having a distal tip extending distally past the distal tip of the hollow aspiration cannula, and a second handle coupled to the proximal end of the coring cannula, and a trocar means extending substantially coaxially through the hollow coring cannula and having a distal tip extending distally past the distal tip of the hollow coring cannula, and a third handle coupled to the proximal end of the trocar means, said method comprising:

a) with the biopsy needle assembly assembled, forcing at least the distal end of said trocar means into and through a cortical bone layer of said bone;

b) removing the trocar means from the biopsy needle assembly by sliding the trocar means out of the hollow coring cannula;

c) moving the remaining hollow aspiration cannula with the hollow coring cannula coaxially therein in said bone to obtain a bone marrow core sample;

d) removing the hollow coring cannula with the bone marrow core sample therein by sliding the coring cannula with the bone marrow core sample out of the hollow aspiration cannula;

e) attaching aspiration means to the hollow aspiration cannula; and f) aspirating said bone to obtain an aspirated bone marrow biopsy sample.

20. A method according to claim 19, wherein:
said step of removing said trocar means comprises lifting said first handle while holding one of said second and third handles in place.

21. A method according to claim 20, wherein:
said step of removing said hollow coring cannula comprises lifting said second handle while holding said third handle in place.

22. A method according to claim 19, wherein:
said step of moving comprises rotating said remaining hollow aspiration cannula with the hollow coring cannula coaxially therein while pushing to effect a screw-like turning.

23. A method according to claim 19, wherein:
said step of forcing comprises gripping a top surface of said first handle and a bottom surface of said third handle and pushing.

* * * * *